United States Patent [19]

Daneshtalab et al.

[11] Patent Number: 5,026,848
[45] Date of Patent: Jun. 25, 1991

[54] GENERATION OF HETEROARYLOXYALKYL HETEROCYCLES WITH ANTIPICORNAVIRUSES ACTIVITIES

[75] Inventors: Mohsen Daneshtalab; Dai Q. Nguyen; Chan M. Ha; Hiep T. Luu; Laurence M. Tempest, all of Edmonton; Ronald G. Micetich, Sherwood Park, all of Canada

[73] Assignee: Synphar Laboratories Incorporated, Alberta, Canada

[21] Appl. No.: 329,147

[22] Filed: Mar. 27, 1989

[30] Foreign Application Priority Data

Mar. 26, 1988 [GB] United Kingdom ............... 8807275

[51] Int. Cl.$^5$ ............... C07D 413/12; C07D 215/60; C07D 261/06; A61K 41/31
[52] U.S. Cl. ............................... 544/137; 544/140; 544/102; 544/101; 546/104; 546/153; 546/157; 548/202; 548/203; 548/205; 548/206; 548/214; 548/217; 548/221; 548/266.2; 548/247; 548/259; 548/336; 548/341
[58] Field of Search ............... 548/240, 238, 247, 206, 548/335, 272; 514/399, 378

[56] References Cited

U.S. PATENT DOCUMENTS

| | | | |
|---|---|---|---|
| 3,682,951 | 8/1972 | Kreider | 548/341 |
| 4,000,302 | 12/1976 | Black et al. | 424/273 |
| 4,146,717 | 3/1979 | Yanamoto et al. | 544/284 |
| 4,171,365 | 10/1979 | Diana et al. | 546/279 |
| 4,268,678 | 5/1981 | Diana et al. | 548/247 |
| 4,451,476 | 5/1984 | Diana et al. | 548/247 |
| 4,857,539 | 8/1989 | Diana | 548/336 |

FOREIGN PATENT DOCUMENTS

| | | |
|---|---|---|
| 0207453 | 1/1987 | European Pat. Off. . |
| 280017 | 1/1987 | European Pat. Off. ............ 548/234 |
| 0137242 | 4/1987 | European Pat. Off. . |
| 2834322 | 2/1979 | Fed. Rep. of Germany . |
| 2098593 A | 11/1982 | United Kingdom . |

OTHER PUBLICATIONS

Chemical Abstracts, "Pharmacodynamics", Jun. 8, 1987, vol. 94, No. 23, p. 35.
Chemical Abstracts, "Heterocycles", Jul. 20, 1981, vol. 95, No. 3, p. 685.
Chemical Abstracts, "Heterocycles", Feb. 14, 1983, vol. 98, No. 7, p. 661.
Chemical Abstracts, Oct. 8, 1984, vol. 101, No. 15, p. 300.
Antimicrobial Agents and Chemotherapy, "In Vitro and In Vivo Activities of WIN 54954, a New Broad-Spectrum Antipicornavirus Drug", Dec. 1989, vol. 33, No. 12, pp. 2069-2074.
J. Med. Chem., "Enantiomeric Effects of Homologues of Disoxaril on the Inhibitory Activity Against Human Rhinovirus-14", 1988, vol. 31, pp. 540-544.
Science, "The Site of Attachment in Human Rhinovirus 14 for Antiviral Agents that Inhibit Uncoating", Sep. 19, 1986, vol. 233, pp. 1286-1293.
Antimicrobial Agents and Chemotherapy, "In Vitro Activity of WIN 51711, a New Broad-Spectrum Antipicornavirus Drug", Jun. 1985, vol. 27, No. 6, pp. 883-886.
J. Med. Chem., "Isoxazoles with Antipicornavirus Activity", 1985, vol. 28, pp. 748-752.
Antiviral Research, "The Structure of Antiviral Agents that Inhibit Uncoating when Complexed with Viral Capsids", 11 (1989), pp. 3-14.
J. Med. Chem., "Synthesis and Structure-Activity Studies of Some Disubstituted Phenylisoxazoles Against Human Picornavirus", 1989, vol. 32, No. 2, pp. 450-455.

Primary Examiner—Jane T. Fan
Assistant Examiner—Celia Chang
Attorney, Agent, or Firm—Armstrong, Nikaido, Marmelstein, Kubovcik & Murray

[57] ABSTRACT

A heteroaryloxyalkylheterocyclic derivative of the Formula I:

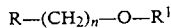

R—(CH$_2$)$_n$—O—R$^1$                I is provided wherein:
R is a non-fused azole moiety;
n is 5, 6, 7 or 8; and
R$^1$ is a non-fused or fused substituted azole, azine, furyl or polycyclic hydrocarbon.

39 Claims, No Drawings

GENERATION OF HETEROARYLOXYALKYL HETEROCYCLES WITH ANTIPICORNAVIRUSES ACTIVITIES

FIELD OF THE INVENTION

The present invention relates to novel heteroaryloxyalkylheterocycles and to their use primarily as antipicornavirus agents.

BACKGROUND OF THE INVENTION

It is well known that the arildone class of compounds exhibit antipicornavirus activity and in particular antirhinoviral activity.

Exemplary compounds of this class have been disclosed in U.S. Pat. No. 4,171,365; and European Patent Applications 0 111 345 and 0 137 242.

Of particular interest are the disclosures of T. J. Smith et al. in Science, 1986, 233, 1286 and G. D. Diana et al. in S. Med. Chem, 1989 23, 450.

SUMMARY OF THE INVENTION

In accordance with the present invention there is provided a heteroaryloxyalkylheterocycle derivative having the general formula:

$$R-(CH_2)_n-O-R^1 \qquad I$$

wherein
R is a non-fused azole moiety;
n is 5, 6, 7, or 8;
$R^1$ is a non-fused or fused substituted azole, azine, furyl or polycyclic hydrocarbon.

More specifically, there is provided a heteroaryloxyalkylheterocycle derivative of the Formula I wherein:
R is preferably selected from the group comprising 3-methyl-5-isoxazolyl; 4-methylthiazol-2-yl; 4-methylisothiazol-5-yl; 3,5-dimethylpyrazol-1-yl; 1-phenylpyrazol-5-yl; 4-chloro-1-phenylpyrazol-5-yl; -5-isothiazolyl or 1-imidazolyl;
n is 6 or 7; and
$R^1$ is preferably selected from the group comprising: 1-naphthyl; 2-napthyl; 1-benzotriazolyl; napth(1,2-b)1,4-oxazin-4-yl; N-dibenzylamino; 4-(1,2,4-triazol-1-yl)-phenyl; 2-benzoxazolyl, 4-(imidazol-1-yl)phenyl; 2-dibenzofuryl; 1-bornyl; 1-adamantanyl; 4-methylquinolin-2-yl; 2-methylquinolin-4-yl; 2-benzimidazolyl; fluoren-9-yl; 2-carbazolyl; 4-acridyl.

It has been determined that physiologically acceptable compounds of Formula I possess valuable pharmacological properties. More specifically, such compounds exhibit antipicornavirus activity, in particular anti-rhinoviral activity. For example, such compounds may also inhibit viral replication in Coxsaki-A9; Coxsaki-A21; Coxsaki-B1; Coxsaki-B4; Echo-7; Echo-11 and Polio-1.

Thus the compounds of formula I may be utilized as active compounds in medicaments.

DESCRIPTION OF THE PREFERRED EMBODIMENT

The compounds of Formula I are prepared by reacting an ω-haloalkyl substituted azole with an appropriately substituted, fused or non-fused hydroxy azole or azine; hydroxy aromatic or hydroxy polycyclic hydrocarbon or a hydroxylamine derivative. The reaction is carried out in the presence of potassium carbonate in dimethyl formamide or acetone for a period of 2–12 h. The products were purified by elution from a silica gel column using an appropriate solvent system.

All the products of the invention were characterized by their respective nmr, IR spectra and elemental analysis. The relative purity of the compounds was established using HPLC. The antiviral activity of the compounds was determined at the concentrations required for 50% inhibition of the viral growth (MIC 50).

More specifically, an ω-haloalkyl substituted azole having the general formula II.

$$R-(CH_2)_n-Br \qquad II$$

wherein R is selected from the group comprising 3-methylisoxazol-5-yl; 4-methylthiazol-2-yl; 4-methylisothiazol-5-yl; 3,5-dimethylpyrazol-1-yl; 5-isothiazoyl; 1-phenylpyrazol-5-yl; 1-phenyl-4-chloropyrazol-5-yl; or 1-imidazolyl and wherein n has a value of between 5 to 8 is reacted with a compound having the formula III under the conditions described supra.

The substituted hydroxyheterocyclic or polycyclic hydrocarbons of formula III comprise:

$$R^1-OH \qquad III$$

wherein R is 1-napthyl; 2-napthyl; 1-benzotriazolyl; napth(1,2-b)-1,4-oxazin-4-yl; N-dibenzylamino; 4-(1,2,4-triazol-1-yl)phenyl; 2-benzoxazolyl; 4-(imidazol-1-yl)phenyl; 2-dibenzofuryl; 1-bornyl; 1-adamantanyl; 4-methylquinolin-2-yl; 2-methylquinolin-4-yl; 2-benzimidazolyl; fluoren-9-yl; 2-carbazolyl or 4-acridyl.

The compounds of formula II may be prepared by reacting the appropriate lithium or sodium salt of the 3,5-dimethylisoxazole; 4-methylthiazol; 4-methylisothiazol; 3,5-dimethylpyrazol; 5-isothiazolyl; 1-phenylpyrazol; 1-phenyl-4-chloropyrazole or 1-imidizolyl with a suitable ω-dihaloalkane. Such dihaloalkanes could be selected from the group comprising 1,6-dibromohexane; 1,5-dibromopentane; 1,7-dibromoheptane. The reaction was carried out in tetrahydrofuran (THF) at −70° C. The products were purified by elution on a silica gel column using suitable solvent systems. The yields varied from 30% to 60%.

Alternatively, the compounds of formula I can be prepared by the alkylation of a suitable hydroxyheterocycle selected from the group comprising 1-napthol; 2-napthol; 1-hydroxybenzotriazole; 4-hydroxynaptho(1,2-b)1,4-oxazin-3-one; N,N-dibenzylhydroxylamine; 4-(1,2,4-triazol-1-yl)phenol; 2-hydroxybenzoxazole; 4-(imidazol-1-yl)phenol; 2-hydroxydibenzofurane; 1-borneol; 1-adamantanol; 2-hydroxy-4-methyl quinoline; 4-hydroxy-2-methylquinoline; 2-hydroxybenzimidazole; 9-hydroxyfluorene; 2-hydroxycarbazole or 4-hydroxy-acridine with 1,6-dibromohexane in a suitable solvent to thereby provide an ω-bromoalkoxy derivative of the formula IV.

The ω-bromoalkoxy derivatives having formula IV are given here below.

$$R^1-O-(CH_2)_n-Br \qquad IV$$

wherein $R^1$ is a moiety selected from the group comprising 1-napthyl; 2-napthyl; 1-benzotriazolyl; napth(1,2-b)-1,4-oxazin-4-yl; N-dibenzylamino; 4-(1,2,4-triazol-1-yl)phenyl; 2-benzoxazolyl; 4-

(imidazol-1-yl)-phenyl; 2-dibenzofuryl; 1-bornyl; 1-adamantanyl; 4-methylquinolin-2-yl; 2-methylquinolin-4-yl; 2-benzimidazolyl; fluoren-9-yl; 2-carbazolyl; or 4-acridyl.

n is 5, 6, or 7.

Compounds of the formula IV are reacted with the appropriate lithium or sodium salt of an azole selected from the group consisting of 3,5-dimethylisoxazole; 4-methylthiazole; 4-methylisothiazole; 3,5-dimethylpyrazole; isothiazole; 1-phenylpyrazole; 1-phenyl-4-chloropyrazole; and imidazole, in a suitable solvent, to give compounds of formula I, respectively.

In summary the compounds of formula I can be prepared by reacting compounds of formula II with a suitable derivative of formula III.

Or, alternatively compounds of formula IV are reacted with a lithium or sodium salt of a suitable azole.

The selected compounds of this invention were tested for anti-rhinoviral activity and other potential pharmacological activity in accordance with known techniques.

More particularly, 5[7-([4(1,2,4-triazol-1-yl)phenoxy]heptyl]-3-methylisoxazole; 5-[7-(2-dibenzofuroxy)heptyl]-3-methylisoxazole; 5-[7-(2,3-dihydro-3-oxo-4H-naphth[1,2-b]-1,4-oxazin-4-yl]-3-methylisoxazole; 5-[7-(carbazol-2-yl)oxyheptyl]-3-methylisoxazole; 5-[7-(2-methylquinolin-4-yl)oxyheptyl]-3-methylisoxazole; 5-[7-(2-dibenzofuroxy)heptyl]-3-methylisoxazole; 2-[7-(2-methylquinolin-4-yl)oxyheptyl]-4-methylthiazole; 5-[6-(2-dibenzofuroxy)hexyl]isothiazole; 5-[6-(2-methylquinolin-4-yl)oxyhexyl]isothiazole; 5-[6-(2-methylquinolin-4-yl)oxyhexyl]-4-methylisothiazole; 5-[6-(2-dibenzofuroxy)hexyl]-4-methylisothiazole; 5-[7-(2-napthyloxy)heptyl]-3-methylisoxazole; 5-[7-(fluoren-9-yl)oxyheptyl]-3-methylthiazole; 5-[7-(1-napthyloxy)heptyl]-3-methylisoxazole; 5-[6-(1-napthyloxy)hexyl]-4-methylisoxazole; 5-[6-(2-dibenzofuroxy)hexyl]-1-phenylpyrazole; 5-[6-(2-methylquinolin-4-yl)-oxyhexyl]-1-phenylpyrazole; 5-[6-(1-napthyloxy)hexyl]-1-phenylpyrazole; 5-[6-(2-napthyloxy)hexyl]-1-phenylpyrazole; 5-[6-(2-dibenzofuroxy)hexyl]-4-chloro-1-phenylpyrazole and 5-[6-(2-methylquinolin-4-yl)oxyhexyl]-4-chloro-1-phenylpyrazole; all demonstrated remarkably inhibitory activity against HRV-1A and HRV-39 in vitro.

More particularly, 5-[7-(2-dibenzofuroxy)heptyl]-3-methylisoxazole; 5-[7-(2-methylquinolin-4-yl)oxyheptyl]-3-methylisoxazole; 2-[7-(2-dibenzofuroxy)heptyl]-4-methylthiazole; 5-[6-(2-dibenzofuroxy)hexyl]-4-methyl isothiazole; 5-[6-(2-dibenzofuroxy)hexyl isothiazole; 2-[6-(2-dibenzofuroxy)hexyl]-4-methylthiazole were tested against 20 serotypes of rhinovirus (namely HRV's 1A, 1B, 2, 4, 15, 17, 23, 29, 30, 31, 32, 36, 39, 44, 49, 53, 56, 63, 86, and 88. These compounds exhibited MIC-50's which varied from 0.5 μg/ml to 25 μg/ml.

When compared to Disoxaril, a candidate compound prepared by Sterling Winthrop, several of the compounds named herein showed less toxicity and better activity as antirhinoviral agents.

Compounds 5-[7-(2-dibenzofuroxy)heptyl]-3-methylisoxazole; 5-[7-(2-methylquinolin-4-yl)oxyheptyl]-3-methylisoxazole; 2-[7-(2-dibenzofuroxy)heptyl]-4-methylthiazole; 5-[6-(2-dibenzofuroxy)hexyl]-4-methylisothiazole; 5-[6-(2-dibenzofuroxy)hexyl]isothiazole; and 2-[6-(2-dibenzofuroxy)hexyl]-4-methylthiazole showed remarkable inhibitory activity against the members of the Entero virus family such as Polio-1; Coxsaki-A9; A22, B1 and B4; and Echo 7 and 11. The MIC 50's of said compounds ranged from 5 μg/ml to 25 μg/ml.

EXAMPLE 1

5-{7-[4-(imidazol-1-yl)phenoxy]-heptyl}-3-methylisoxazole (1)

R = 3-methylisoxazol-5-yl
n = 7
R$^1$ = 4-(imidazol-1-yl)phenyl.

7-(3-methylisoxazol-5-yl)heptyl bromide (520 mg, 0.002 mol) was added to a mixture of p-(imidazol-1-yl)phenol (320 mg, 0.002 mol) and potassium carbonate (276 mg, 0.002 mol) in anhydrous acetone (20 ml) while stirring. The mixture was heated under reflux for 27 hours and the solid portion was taken out by filtration. After concentration under reduced pressure, the residual oil was dissolved in dichloromethane (30 ml), washed with distilled water (3×20 ml), then with a 5% aqueous solution of potassium hydroxide (30 ml) and again with distilled water (3×20 ml). The resulting crude compound was, then, purified by elution from a silica gel column using methanolhexane-ethyl acetate (1:3:7 v/v) as eluant to give 5-[7-(4-imidazol-1-yl)heptyl]-3-methylisoxazole as a pale yellow solid (yield 50%, m.p. 57°-58° C.).

NMR (CDCl$_3$) 1.39-1.89 (m, 10H, -(CH$_2$)$_5$), 2.30 (S, 3H, CH$_3$-Het), 2.74 (t, J=9 Hz, 2H, CH$_2$-Het), 4.03 (t, J=9 Hz, 2H, CH$_2$-O), 5.85 (S, 1H, H-Het), 6.97-7.35 (m, 6H, H-Ar-Het), 7.80 (S, 1H, H-Het).

C$_{20}$H$_{25}$N$_3$O$_2$: Analysis found: C, 70.85; H, 7.49; N, 12.31. Required: C, 70.76; H, 7.42; N, 12.38.

SCHEMATIC FOR EXAMPLE 1

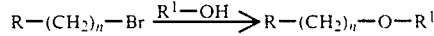

R = 3-methylisoxazol-5-yl
n = 7
R$^1$ = 4-(imidazol-1-yl)phenyl

By procedures similar to those used in Example 1, and starting with the appropriately substituted five-membered heterocyclic moiety R and R$^1$, the following compounds were prepared.

EXAMPLE 2

5-{7-[(benzoxazol-2-yl)oxy]heptyl}-3-methylisoxazole (2)

R = 3-Methylisoxazol-5-yl
n = 7
R$^1$ = 2-Benzoxazolyl.

Light yellow solid, (75%), m.p. 68°-70° C.,
NMR (CDCl$_3$) 1.32-1.87 (m, 10H, -(CH$_2$)$_5$), 2.28 (S, 3H, CH$_3$-Het), 2.70 (t, J=9 Hz, 2H, H-Het), 3.85 (t, J=9 Hz, 2H, H-O), 5.8 (S, 1H, H-Het) 6.97-7.30 (m, 4H, H-Ar).

C$_{18}$H$_{22}$N$_2$O$_2$: Analysis found: C, 68.85; H, 7.12; N, 8.83. Required: C, 68.77; H, 7.05; N, 8.91.

EXAMPLE 3

5-{7-[4-(1,2,4-triazol-1-yl)phenoxy]heptyl}-3-methylisoxazole (3)

R = 3-methylisoxazol-5-yl
n = 7
R$^1$ = 4-(1,2,4-triazol-1-yl)phenyl.
White powder, (59%), m.p. 95°-96° C.

NMR (CDCl₃) 1.35–1.89 (m, 10H, -(CH₂)₅, 2.28 (S, 3H, CH₃-Het), 2.72 (t, J=9 Hz, 2H, CH₂-Het), 4.01 (t, J=9 Hz, 2H, CH₂-O), 5.82 (S, 1H, H-Het), 6.89–7.63 (m, 4H, H-Ar), 8.1 (S, 1H, H-triazole), 8.48 (S, 1H, H-triazole).

C₁₉H₂₄N₄O₂: Analysis found: C, 67.11; H, 7.19; N, 16.39. Required: C, 67.03; H, 7.11; N, 16.46.

EXAMPLE 4

5-[7-(N,N-dibenzylaminoxy)heptyl]-3-methylisoxazole (4)

R = 3-methylisoxazol-5-yl
n = 7
R¹ = N,N-dibenzylamine.
White solid, (48.5%), m.p. 114°–116° C.

NMR (CDCl₃) 1.30–1.91 (m, 10H, -(CH₂)₅), 2.26 (S, 3H, CH₃-Het), 2.70 (t, J=9 Hz, 2H, CH₂-Het), 3.42 (t, J=9 Hz, 2H, CH₂-O), 3.68 (S, 4H, CH₂-N), 5.81 (S, 1H, H-Het), 7.23–7.36 (m, 10H, H-Ar).

C₂₅H₃₂N₂O₂: Analysis found: C, 76.61; H, 8.29; N, 7.06. Required: C, 76.50; H, 8.22; N, 7.14.

EXAMPLE 5

5-[7-(2-dibenzofuroxy)heptyl]-3-methylisoxazole (5)

R = 3-methylisoxazol-5-yl
n = 7
R¹ = 2-dibenzofuryl.
White solid, (55%), m.p. 72°–74° C.

NMR (CDCl₃) 1.30–1.87 (m, 10H, -(CH₂)₅), 2.26 (S, 3H, CH₃-Het), 2.69 (t, J=9 Hz, 2H, CH₂-Het), 4.04 (t, J=9 Hz, 2H, CH₂-O), 5.80 (S, 1H, H-Het), 7.02–7.93 (m, 7H, H-Ar).

C₂₃H₂₅NO₃: Analysis found: C, 76.12; H, 6.97; N, 3.78. Required: C, 76.01; H, 6.93; N, 3.85.

EXAMPLE 6

5-[7-(2,3-dihydro-3-oxo-4H-napth[1,2-b]-1,4-oxazin-4-yl)oxyheptyl]-3-methylisoxazole (6)

R = 3-methylisoxazol-5-yl
n = 7
R¹ = 2,3-dihydro-3-oxo-4H-napth[1,2-b]-1,4-oxazin-4-yl.
Light brown solid, (50%), m.p. 65°–67° C., IR (neat) 1706 cm⁻¹ (m, c=o).

NMR (CDCl₃) 1.40–1.90 (m, 10H, -(CH₂)₅), 2.28 (S, 3H, CH₃-Het), 2.73 (t, J=9 Hz, 2H, CH₂-Het), 4.19 (t, J=8 Hz, 2H, CH₂-O), 4.87 (S, 2H, cyclic-CH₂), 5.84 (S, 1H, H-Het), 7.44–8.12 (m, 6H, H-Ar).

C₂₃H₂₆N₂O₄: Analysis found: C, 70.11; H, 6.71; N, 7.02. Required: C, 70.04; H, 6.64; N, 7.10.

EXAMPLE 7

1-[6-(benzotriazol-1-yloxy)hexyl]-3,5-dimethylpyrazole (7)

R = 3,5-dimethylpyrazol-1-yl
n = 6
R¹ = 1-benzotriazolyl.
Pale yellow oil, (60%).

NMR (CDCl₃) 1.36–1.92 (m, 8H, -(CH₂)₄), 2.23 (S, 6H, CH₃-Het), 4.00 (t, J=9 Hz, 2H, CH₂-Het), 4.53 (t, J=9 Hz, 2H, CH₂-O), 5.80 (S, 1H, H-Het), 7.38–8.05 (m, 4H, H-Ar).

C₁₇H₂₃N₅O: Analysis found: C, 65.21; H, 7.49; N, 22.24. Required: C, 65.15; H, 7.40; N, 22.35.

EXAMPLE 8

5-[7-(carbazol-2-yl)oxyheptyl]-3-methylisoxazole (8)

R = 3-methylisoxazol-5-yl
n = 7
R¹ = 2-carbozolyl.
White solid, (20%), m.p. 160°–162° C., IR (neat) 3495 cm⁻¹ (N-H).

NMR (CDCl₃) 1.39–1.93 (m, 10H, -(CH₂)₅), 2.28 (S, 3H, CH₃-Het), 2.72 (t, J=9 Hz, 2H, CH₂-Het), 4.07 (t, J=9 Hz, 2H, CH₂-O), 5.84 (S, 1H, H-Het), 6.84–8.15 (m, 7H, H-Ar).

C₂₃H₂₆N₂O₂: Analysis found: C, 76.32; H, 7.28; N, 7.65. Required: C, 76.21; H, 7.23; N, 7.73.

EXAMPLE 9

5-[7-(2-methylquinolin-4-yl)oxyheptyl]-3-methisoxazole (9)

R = 3-methylisoxazol-5-yl
n = 7
R¹ = 2-methylquinolin-4-yl.
White solid, (60%), m.p. 80°–82° C.

NMR (CDCl₃) 1.27–1.90 (m, 10H, -(CH₂)₅), 2.16 (S, 3H, CH₃-Het), 2.59 (S, 3H, CH₃-quinoline), 2.68 (t, J=9 Hz, 2H, CH₂-Het), 4.22 (t, J=9 Hz, 2H, CH₂-O), 6.08 (S, 1H, H-Het), 6.90 (S, 1H, H-quinoline), 7.43–8.08 (m, 4H, H-quinoline).

C₂₁H₂₆N₂O₂: Analysis found: C, 74.61; H, 7.80; N, 8.21. Required: C, 74.53; H, 7.74; N, 8.28.

EXAMPLE 10

5-[7-(4-methylquinolin-2-yl)oxyheptyl]-3-methylisoxazole (10)

R = 3-methylisoxazol-5-yl
n = 7
R¹ = 4-methylquinolin-2-yl.
White solid, (20%), m.p. 205°–207° C.

NMR (CDCl₃) 1.29–1.90 (m, 10H, -(CH₂)₅), 2.26 (S, 3H, CH₃-Het), 2.52–2.75 (m, 5H, CH₂-Het and CH₃-quinoline), 4.44 (t, J=9 Hz, 2H, CH₂-O), 5.78 (S, 1H, H-Het), 6.73 (S, 1H, H-quinoline), 7.28–7.94 (m, 4H, H-Ar).

C₂₁H₂₆N₂O₂: Analysis found: C, 74.61; H, 7.70; N, 8.36. Required: C, 74.53; H, 7.74; N, 8.28.

EXAMPLE 11

5-[7-(benzimidazol-2-yl)oxyheptyl]-3-methylisoxazole (11)

R = 3-methylisoxazol-5-yl
n = 7
R¹ = benzimidazol-2-yl.
White solid, (16%), m.p. 120°–121° C., IR (neat) 3135 cm⁻¹ (m, N-H).

NMR (CDCl₃) 1.28–1.92 (m, 10H, -(CH₂)₅), 2.29 (S, 3H, CH₃-Het), 2.71 (t, J=9 Hz, 2H, CH₂-Het), 3.91 (t, J=9 Hz, 2H, CH₂-O), 5.80 (S, 1H, H-Het), 6.93–7.30 (m, 4H, H-Ar).

C₁₈H₂₃N₃O₂: Analysis found: C, 69.05; H, 7.45; N, 13.36. Required: C, 68.98; H, 7.40; N, 13.41.

EXAMPLE 12

5-[7-(Adamantanol-1-yl)oxyheptyl]-3-methylisoxazole (12)

R = 3-methylisoxazol-5-yl
n = 7
R¹ = Adamantan-1-yl.

Catalyst: sodamide (excess); solvent: toluene.
Yellow oil, (20%).

NMR (CDCl$_3$) 1.30–2.22 (m, 24H, -(CH$_2$)$_5$ and Adamantanol Hydrogen), 2.30 (S, 3H, CH$_3$-Het), 2.69 (t, J=9 Hz, 2H, CH$_2$-O), 3.40 (t, J=9 Hz, 2H, CH$_2$-O) 5.85 (S, 1H, H-Het).

C$_{21}$H$_{33}$NO$_2$: Analysis found: C, 76.12; H, 10.08; N, 4.18. Required: C, 76.09; H, 10.03; N, 4.23.

EXAMPLE 13

5-[7-(2-naphthyl)oxyheptyl]-3-methylisoxazole (13)

R = 3-methylisoxazol-5-yl
n = 7
R$^1$ = 2-naphthyl.
White solid, (75%), m.p. 48°–50° C.

NMR (CDCl$_3$) 1.20–1.96 (m, 10H, -(CH$_2$)$_5$), 2.26 (S, 3H, CH$_3$-Het), 2.72 (t, J=9 Hz, 2H, CH$_2$-Het), 4.07 (t, J=9 Hz, 2H, CH$_2$-O), 5.80 (S, 1H, H-Het), 7.10–8.87 (m, 7H, H-Ar).

C$_{21}$H$_{25}$NO$_2$: Analysis found: C, 78.10; H, 7.84; N, 4.27. Required: C, 77.98; H, 7.79; N, 4.33.

EXAMPLE 14

5-[7-(1-naphthyl)oxyheptyl]-3-methylisoxazole (14)

R = 3-methylisoxazol-5-yl
n = 7
R$^1$ = 1-naphthyl.
Light yellow solid, (59%), m.p. 79°–81° C.

NMR (CDCl$_3$) 1.34–2.05 (m, 10H, -(CH$_2$)$_5$), 2.23 (S, 3H, CH$_3$-Het), 2.69 (t, J=9 Hz, 2H, CH$_2$-Het), 4.12 (t, J=9 Hz, 2H, CH$_2$-O), 5.77 (S, 1H, H-Het), 6.72–8.36 (m, 7H, H-Ar).

C$_{21}$H$_{25}$NO$_2$: Analysis found: C, 74.37; H, 7.47; N, 4.08; S, 9.36. Required: C, 74.30; H, 7.42; N, 4.13; S, 9.44.

EXAMPLE 15

5-[7-(2-dibenzofuroxy)heptyl]-3-methylthiazole (15)

R = 3-methylthiazol-5-yl
n = 7
R$^1$ = 2-dibenzofuryl.
Pale yellow solid, (42%), m.p. 48°–50° C.

NMR (CDCl$_3$) 1.23–1.92 (m, 10H, -(CH$_2$)$_5$), 2.37 (S, 3H, CH$_3$-Het), 2.95 (t, J=9 Hz, 2H, CH$_2$-Het), 4.02 (t, J=9 Hz, 2H, CH$_2$-O), 6.67 (S, 1H, H-Het), 6.97–7.87 (m, 7H, H-Ar).

C$_{23}$H$_{25}$NO$_2$S; Analysis found: C, 72.87; H, 6.71; N, 3.62; S, 8.41. Required: C, 72.79; H, 6.64; N, 3.69; S, 8.45.

EXAMPLE 16

5-[7-(2-methylquinoline-4-yl)oxyheptyl]-3-methylthiazole (16)

R = 3-methylthiazole-5-yl
n = 7
R$^1$ = 2-methylquinolin-4-yl.
Pale yellow solid, (64%), m.p. 60°–61° C.

NMR (CDCl$_3$) 1.38–2.00 (m, 10H, -(CH$_2$)$_5$), 2.40 (S, 3H, -CH$_3$-Het), 2.67 (S, 3H, CH$_3$-quinoline), 2.92–3.04 (t, J=9 Hz, 2H, CH$_2$-Het), 4.10–4.22 (t, J=9 Hz, 2H, CH$_2$-O), 6.60 (S, 1H, H-quinoline), 6.70 (S, 1H, H-Het), 7.37–8.20 (m, 4H, H-quinoline).

C$_{21}$H$_{26}$N$_2$OS: Analysis found: C, 71.23; H, 7.45; N, 7.85; S, 9.01. Required: C, 71.15; H, 7.39; N, 7.90; S, 9.04.

EXAMPLE 17

5-[7-(4-methylquinolin-2-yl)oxyheptyl]-3-methylthiazole (17)

R = 3-methylthiazol-5-yl
n = 7
R$^1$ = 4-methylquinolin-2-yl.
Pale yellow solid, (23%), m.p. 35°–36° C.

NMR (CDCl$_3$) 1.35–1.92 (m, 10H, -(CH$_2$)$_5$), 2.42 (S, 3H, CH$_3$-Het), 2.61 (S, 3H, CH$_3$-quinoline), 2.92–3.04 (t, J=9 Hz, 2H, CH$_2$-Het), 4.39–4.50 (t, J=9 Hz, 2H, CH$_2$-O), 6.70s, 1H, H$_3$-quinoline), 6.75 (S, 1H, H-Het), 7.33–7.90 (m, 4H, H-quinoline).

C$_{21}$H$_{26}$N$_2$OS: Analysis found: C, 71.27; H, 7.45; N, 7.82; S, 8.97. Required: C, 71.15; H, 7.39; N, 7.90; S, 9.04.

EXAMPLE 18

5-[7-(2-Naphthyl)oxyheptyl]-3-methylthiazole (18)

R = 3-methylthiazol-5-yl
n = 7
R$^1$ = 2-naphthyl.
Thick yellow oil, (66%).

NMR (CDCl$_3$) 1.28–1.93 (m, 10H, -(CH$_2$)$_5$), 2.41 (S, 3H, CH$_3$-Het), 2.94 (t, J=9 Hz, 2H, CH$_2$-Het), 4.04 (t, J=9 Hz, 2H, CH$_2$-O), 6.68 (S, 1H, H-Het), 7.06–7.77 (m, 7H, H-Ar).

C$_{21}$H$_{25}$NOS: Analysis found: C, 74.41; H, 7.47; N, 4.09; S, 9.41. Required: C, 74.30; H, 7.42; N, 4.13; S, 9.44.

EXAMPLE 19

5-[6-(2-dibenzofuroxy)hexyl]-4-methylisothiazole (19)

R = 4-methylisothiazol-5-yl
n = 6
R$^1$ = 2-dibenzofuryl.
White solid, (25%), m.p. 65°–67° C.

NMR (CDCl$_3$) 1.33–1.88 (m, 8H, -(CH$_2$)$_4$), 2.14 (S, 3H, CH$_3$-Het), 2.78 (t, J=9 Hz, 2H, CH$_2$-Het), 3.99 (t, J=9 Hz, 2H, CH$_2$-O), 6.95–7.92 (m, 7H, H-Ar), 8.18 (S, 1H, H-Het).

C$_{22}$H$_{23}$NO$_2$S: Analysis found: C, 72.00; H, 6.39; N, 3.79; S, 8.70. Required: C, 72.30; H, 6.34; N, 3.83; S, 8.77.

EXAMPLE 20

5-[6-(2-methylquinolin-4-yl)oxyhexyl]-4-methylisothiazole (20)

R = 4-methylisothiazol-5-yl
n = 6
R$^1$ = 2-methylquinolin-4-yl.
Yellow solid, (41%), m.p. 66°–67° C.

NMR (CDCl$_3$) 1.35–2.01 (m, 8H, -(CH$_2$)$_4$), 2.15 (S, 3H, CH$_3$-Het), 2.66 (S, 3H, CH$_3$-quinoline), 2.79 (t, J=9 Hz, 2H, CH$_2$-Het), 4.12 (t, J=9 Hz, 2H, CH$_2$-O), 6.58 (S, 1H, H-quinoline), 7.35–8.18 (m, 5H, H-Het and H-quinoline).

C$_{20}$H$_{24}$N$_2$OS: Analysis found: C, 70.67; H, 7.15; N, 8.19; S, 9.34. Required: C, 70.55; H, 7.10; N, 8.23; S, 9.42.

EXAMPLE 21

5-[6-(2-napthyl)oxyhexyl]-4-methylisothiazole (21)

R = 4-methylisothiazol-5-yl
n = 6
R$^1$ = 2-napthyl.

White solid, (70%), m.p. 64°-66° C.

NMR (CDCl$_3$) 1.38-1.92 (m, 8H, -(CH$_2$)$_4$), 2.17 (S, 3H, CH$_3$-Het), 2.80 (t, J=9 Hz, 2H, CH$_2$-Het), 4.06 (t, J=9 Hz, 2H, CH$_2$-O), 7.08-7.77 (m, 7H, H-Ar), 8.18 (S, 1H, H-Het).

C$_{20}$H$_{23}$NOS: Analysis found: C, 73.92; H, 7.16; N, 4.26; S, 9.84. Required: C, 73.81; H, 7.12; N, 4.30; S, 9.85.

EXAMPLE 22

5-[6-(1-napthyl)oxyhexyl]-4-methylisothiazole (22)

R=4-methylisothiazol-5-yl
n=6
R$^1$=1-napthyl.

Light yellow solid, (64%), m.p. 52°-54° C.

NMR (CDCl$_3$) 1.34-1.95 (m, 8H, -(CH$_2$)$_4$), 2.12 (S, 3H, CH$_3$-Het), 2.73 (t, J=9 Hz, 2H, CH$_2$-Het), 4.05 (t, J=9 Hz, 2H, CH$_2$-O), 6.68-8.33 (m, 8H, H-Het and H-Ar).

C$_{20}$H$_{23}$NOS: Analysis found: C, 73.89; H, 7.18; N, 4.25; S, 9.79. Required: C, 73.81; H, 7.12; N, 4.30; S, 9.85.

EXAMPLE 23

1-[6-(2,3-dihydro-3-oxo-4H-napth[1,2-b]-1,4-oxazine-4-yl)oxyhexyl]-3,5-dimethylpyrazole (23)

R=3,5-dimethylpyrazol-1-yl
n=6
R$^1$=2,3-dihydro-3-oxo-4H-napth[1,2-b]-1,4-oxazine-4-yl.

Thick brown oil, (15%), IR (neat) 1705 cm$^{-1}$ (c=o).

NMR (CDCl$_3$) 1.34-1.91 (m, 8H, -(CH$_2$)$_4$), 2.23 (S, 6H, CH$_3$-Het), 3.97 (t, J=9 Hz, 2H, CH$_2$-Het), 4.17 (t, J=8 Hz, 2H, CH$_2$-O), 4.86 (S, 2H, cyclic-CH$_2$), 5.80 (S, 1H, H-Het); 6.42-7.13 (m, 6H, H-Ar).

C$_{23}$H$_{27}$N$_3$O$_3$: Analysis found: C, 70.31; H, 6.97; N, 10.62. Required: C, 70.21; H, 6.92; N, 10.68.

EXAMPLE 24

1-[6-(2-dibenzofuroxy)hexyl]-3,5-dimethylpyrazol (24)

R=3,5-dimethylpyrazol-1-yl
n=6
R$^1$=2-dibenzofuryl.

Light yellow solid, (47%), m.p. 49°-51° C.

NMR (CDCl$_3$) 1.25-1.95 (m, 8H, -(CH$_2$(4)), 2.24 (S, 6H, CH$_3$-Het), 3.90-4.09 (m, 4H, CH$_2$-Het and CH$_2$-O), 5.77 (S, 1H, H-Het), 6.96-7.94 (m, 7H, H-Ar).

C$_{23}$H$_{26}$N$_2$O$_2$: Analysis found: C, 76.33; H, 7.28; N, 7.65. Required: C, 76.21; H, 7.23; N, 7.73.

EXAMPLE 25

5-[6-(2-dibenzofuroxy)hexyl]isothiazole (25)

R=isothiazol-5-yl
n=6
R$^1$=2-dibenzofuryl.

Yellow solid, (64%), m.p. 30°-31° C.

NMR (CDCl$_3$) 1.33-1.92 (m, 8H, -(CH$_2$)$_4$), 2.93 (t, J=9 Hz, 2H, CH$_2$-Het), 4.02 (t, J=9 Hz, 2H, CH$_2$-O), 6.94-7.93 (m, 8H, H-Het and H-Ar) 8.32-8.38 (d, J=18 Hz, C$_3$-H, H-Het).

C$_{21}$H$_{21}$NO$_2$S: Analysis found: C, 71.88; H, 6.09; N, 3.92; S, 9.08. Required: C, 71.77; H, 6.03; N, 3.99; S, 9.12.

EXAMPLE 26

5-[6-(2-methylquinoline-4-yl)oxyhexyl]isothiazole (26)

R=isothiazol-5-yl
n=6
R$^1$=2-methylquinolin-4-yl.

Yellow solid, (33%), m.p. 80°-82° C.

NMR (CDCl$_3$) 1.35-2.03 (m, 8H, -(CH$_2$)$_4$), 2.63 (S, 3H, CH$_3$-quinoline), 2.96 (t, J=9 Hz, 2H, CH$_2$-Het), 4.14 (t, J=9 Hz, 2H, CH$_2$-O), 6.60 (S, 1H, H-quinoline), 6.92-6.99 (d, J=12 Hz, C$_4$-H, H-Het), 7.37-8.16 (m, 4H, H-Ar), 8.30-8.37 (d, J=12 Hz, C$_3$-H, H-Het).

C$_{19}$H$_{22}$N$_2$OS: Analysis found: C, 70.05; H, 6.85; N, 8.53; S, 9.78. Required: C, 69.90; H, 6.79; N, 8.58; S, 9.82.

EXAMPLE 27

2-[6-(2-dibenzofuroxy)hexyl]-4-methylthiazole (27)

R=4-methylthiazol-2-yl
n=6
R$^1$=2-dibenzofuryl.

Pale yellow solid, (55%), m.p. 39°-41° C.

NMR (CDCl$_3$) 1.35-1.87 (m, 8H, -(CH$_2$)$_4$), 2.40 (S, 3H, CH$_3$-Het), 2.94 (t, J=9 Hz, 2H, CH$_2$-Het), 3.99 (t, J=8 Hz, 2H, CH$_2$-O), 6.65 (S, 1H, H-Het), 6.94-7.90 (m, 7H, H-Ar).

C$_{22}$H$_{23}$NO$_2$S: Analysis found: C, 72.41; H, 6.39; N, 3.79; S, 8.70. Required: C, 72.30; H, 6.34; N, 3.83; S, 8.77.

EXAMPLE 28

5-[3-(2-methylquinoline-4-yl)oxypropyl]isothiazole (28)

R=isothiazol-5-yl
n=3
R$^1$=2-methylquinolin-4-yl.

Pale yellow solid, (64%), m.p. 77°-79° C.

NMR (CDCl$_3$) 2.27-2.45 (m, 2H, -CH$_2$-), 2.70 (S, 3H, CH$_3$-quinoline), 3.29 (t, J=9 Hz, 2H, CH$_2$-Het), 4.24 (t, J=9 Hz, 2H, CH$_2$-O), 6.58 (S, 1H, H-quinoline), 7.02-7.12 (d, J=12 Hz, C$_4$-H, H-Het), 7.38-8.22 (m, 4H, H-Ar), 8.36-8.46 (d, J=12 Hz, C$_3$-H, H-Het).

C$_{16}$H$_{16}$N$_2$OS: Analysis found: C, 67.69; H, 5.74; N, 9.81; S, 11.20. Required: C, 67.58; H, 5.67; N, 9.85; S, 11.27.

EXAMPLE 29

5-[7-(fluorene-9-yloxy)-heptyl]-3-methylisoxazole (29)

R=3-methylisoxazol-5-yl
n=7
R$^1$-fluoren-9-yl.

The sodium salt of 9-hydroxyfluorene was made by reacting sodium metal in anhydrous benzene before the etherization with 7-(3-methylisoxazol-5-yl)-heptyl bromide in the same solvent.

Yellow oil, (35%).

NMR (CDCl$_3$) 1.24-1.90 (m, 10H, -(CH$_2$)$_5$), 2.24 (S, 3H, CH$_3$-Het), 2.66 (t, J=9 Hz, 2H, CH$_2$-Het), 3.37 (t, J=9 Hz, 2H, CH$_2$-O), 5.78 (S, 1H, H-Het), 7.23-7.68 (m, 8H, H-Ar).

C$_{24}$H$_{27}$NO$_2$: Analysis found: C, 79.81; H, 7.59; N, 3.82. Required: C, 79.74; H, 7.53; N, 3.87.

EXAMPLE 30

5-[6-(2-dibenzofuroxy)hexyl]-1-phenylpyrazole (30)

R=1-phenylpyrazol-5-yl
n=6

R¹ = 2-dibenzofuryl.
Yellowish oil, (55%).
NMR (CDCl₃) 1.55–1.77 (m, 8H, -(CH₂)₄), 2.62 (t, J=9 Hz, 2H, CH₂-Het), 3.95 (t, J=9 Hz, 2H, CH₂-O), 6.21 (S, 1H, H₄-pyrazole), 6.98–7.89 (m, 13H, aromatic protons).

$C_{27}H_{26}N_2O_2$: Analysis found: C, 79.18; H, 6.45; N, 6.73. Required: C, 79.00; H, 6.38; N, 6.82.

EXAMPLE 31

5-[6-(2-methylquinolin-4-yl)oxyhexyl]-1-phenyl-pyrazole (31)

R = 1-phenylpyrazol-5-yl
n = 6
R¹ = 2-methylquinolin-4-yl.

Yellow prisms, (60%), m.p. 63°–66° C.
NMR (CDCl₃) 1.25–1.91 (m, 8H, -(CH₂)₄), 2.65–2.73 (m, 5H, CH₂-Het and CH₃-Het), 4.12 (t, J=9 Hz, 2H, CH₂-O), 6.22 (S, 1H, H₄-pyrazole), 6.59 (S, 1H, H₃-quinoline), 7.31–8.20 (m, 10H, aromatic protons).

$C_{25}H_{27}N_3O$: Elemental analysis found: C, 77.97; H, 7.16; N, 10.75. Required: C, 77.89; H, 7.06; N, 10.90.

EXAMPLE 32

5-[6-(2-naphthyl)-oxyhexyl]-1-phenylpyrazole (32)

R = 1-phenylpyrazole-5-yl
n = 6
R¹ = 2-naphthyl.

White, fine crystal, (62%), m.p. 77°–79° C.
NMR (CDCl₃) 1.25–1.82 (m, 8H, -(CH₂)₄), 2.64 (t, J=9 Hz, 2H, CH₂-Het), 3.95 (t, J=9 Hz, 2H, CH₂-O), 6.20 (S, 1H, H₄-pyrazole), 7.05–7.75 (m, 13H, aromatic protons).

$C_{25}H_{26}N_2O$: Elemental analysis found: C, 81.17; H, 7.16; N, 7.49. Required: C, 81.05; H, 7.07; N, 7.56.

EXAMPLE 33

5-[6-(1-naphthyl)oxyhexyl]-1-phenylpyrazole (33)

R = 1-phenylpyrazol-5-yl
n = 6
R¹ = 1-naphthyl.

Yellow prisms, (60%), m.p. 44°–46° C.
NMR (CDCl₃) 1.25–1.82 (m, 8H, -(CH₂)₄), 2.62 (t, J=9 Hz, 2H, CH₂-Het), 4.02 (t, J=9 Hz, 2H, CH₂-O), 6.15 (S, 1H, H₄-pyrazole), 6.60–8.27 (m, 13H, aromatic protons).

$C_{25}H_{26}N_2O$: Elemental analysis found: C, 81.21; H, 7.12; N, 7.52. Required: C, 81.05; H, 7.07; N, 7.56.

EXAMPLE 34

1-[6-(2-methylquinolin-4-yl)oxyhexyl]-imidazole (34)

R = imidazol-1-yl
n = 6
R¹ = 2-methylquinolin-4-yl.

Yellow solid, (70%), m.p. 90°–92° C.
NMR (CDCl₃) 1.32–2.03 (m, 8H, -(CH₂)₄), 2.68 (S, 3H, CH₃-quinoline), 3.96 (t, J=9 Hz, 2H, CH₂-Het), 4.16 (t, J=9 Hz, 2H, CH₂-O), 6.59 (S, 1H, H₄ of quinoline), 6.87–8.18 (m, 7H, aromatic protons of imidazole and quinoline).

$C_{19}H_{23}N_2O$: Elemental analysis found: C, 77.33; H, 7.91; N, 9.41. Required: C, 77.25; H, 7.85; N, 9.48.

EXAMPLE 35

4-chloro-5-[6-(2-methylqinolin-4-yl)oxyhexyl]phenyl-pyrazole (35)

R = 4-chloro-1-phenylpyrazol-5-yl
n = 6
R¹ = 2-methylqinolin-4-yl

Colorless prisms, (81%), m.p. 84°–85° C., IR (neat) 1591 cm⁻¹ (C=N), 1100 cm⁻¹ (C-O), 771 cm⁻¹ (c-Cl).
NMR (CDCl₃) 1.30–1.80 (m, 8H, -(CH₂)₄), 2.57 (S, 3H, CH₃-quinoline); 2.65 (t, J=9 Hz, 2H, CH₂-pyrazole), 4.15 (t, J=9 Hz, 2H, CH₂-O), 6.60 (S, 1H, H₃-quinoline), 7.60 (S, 1H, H-pyrazole), 7.35–8.15 (m, 9H, H-aromatic).

$C_{23}H_{26}ClN_3O$: Analysis found: C, 69.84; H, 6.66; N, 10.56; Cl, 8.90. Required: C, 69.77; H, 6.62; N, 10.61; Cl, 8.95.

EXAMPLE 36

4-chloro-5[6-(carbazol-2-yl)oxyhexyl]phenylpyrazole (36)

R = 4-chlorophenylpyrazol-5-yl
n = 6
R¹ = carbazol-2-yl.

Colorless prisms, (80%), m.p. 74°–75° C., IR (neat) 1605 cm⁻¹ (C=N), 1095 cm⁻¹ (C-O), 791 cm⁻¹ (C-Cl).
NMR (CDCl₃) 1.20–1.80 (m, 8H, -(CH₂)₄), 2.65 (t, J=9 Hz, 2H, CH₂-pyrazole), 4.15 (t, J=9 Hz, 2H, CH₂-O, 7.60 (S, 1H, H-pyrazole), 6.84–8.15 (m, 12H, H-aromatic).

$C_{27}H_{26}ClN_3O$: Analysis found: C, 73.15; H, 5.96; N, 9.41; Cl, 7.92. Required: C, 73.04; H, 5.90; N, 9.46; Cl, 7.98.

EXAMPLE 37

4-chloro-5[6-(2-dibenzofuroxy)hexyl]phenylpyrazole (37)

R = 4-chloro-1-phenylpyrazol-5-yl
n = 6
R¹ = 2-dibenzofuryl.

Colorless prisms, (80%), m.p. 63°–64° C., IR (neat) 1591 cm⁻¹ (C=N), 1100 cm⁻¹ (C-O), 771 cm⁻¹ (C-Cl).
NMR (CDCl₃) 1.20–1.80 (m, 8H, -(CH₂)₄), 2.70 (t, J=9 Hz, 2H, CH₂-pyrazole), 3.95 (t, J=9 Hz, 2H, CH₂-O), 6.95–7.95 (m, 13H, H-aromatic).

$C_{27}H_{25}ClN_2O_2$: Analysis found: C, 72.97; H, 5.71; N, 6.24; Cl, 7.99. Required: C, 72.88; H, 5.66; N, 6.30; Cl, 7.97.

EXAMPLE 38

7-(3-methylisoxazol-5-yl)heptyl bromide (38)

R = 3-methylisoxazol-5-yl
n = 7.

To a solution of diisopropylamine (8.4 ml, 0.06 mol) in THF, was added, at −5° C., and under nitrogen, n-butyllithium (1.6M in Hexane, 37.5 ml, 0.06 mole). After the addition was complete, the solution was cooled to −70° C. and 3,5-dimethylisoxazole (5.82 g, 0.06 mol) in THF (20 ml) was added dropwise. The mixture was stirred for an additional hour at −70° C., then added, via nitrogen purge, to a solution of 1,6-dibromohexane (58.56 g, 0.24 mol) in THF (40 ml), and chilled to −70° C. with stirring. The mixture was allowed to gradually warm to room temperature and then stirred overnight. After quenching with saturated solution of ammonium chloride (30 ml), the mixture was extracted with isopropylacetate (250 ml) and the extract was washed with distilled water and dried. Removal of the solvent and excess 1,6-dibromohexane gave an oil which was purified by c.c. (EtAcO/Hexane; 1:4).

Pale yellow oil, (53%).

NMR (CDCl$_3$) 0.80–2.10 (m, 10H, -(CH$_2$)$_5$), 2.30 (S, 3H, CH$_3$-Het), 2.74 (t, J=9 Hz, 2H, H-Het), 3.43 (t, J=9 Hz, 2H, H-Br), 5.85 (S, 1H, H-Het).

C$_{11}$H$_{18}$BrNO: Analysis found: C, 50.84; H, 6.93; N, 5.42; Br, 30.65. Required: C, 50.78; H, 6.97; N, 5.38; Br, 30.71.

Schematic of Example 38

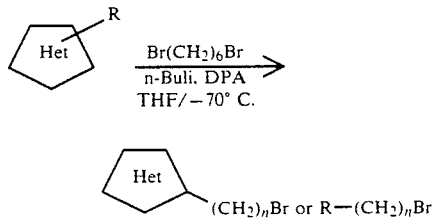

Following the same procedure as example 30, and starting with the appropriate heterocyclic moieties, the following compounds were prepared.

EXAMPLE 39

7-(4-methylthiazol-5-yl)heptyl bromide (39)

R = 3-methylthiazol-5-yl
n = 7.
Light yellow oil, (47%).

NMR (CDCl$_3$) 1.1–2.2 (m, 10H, -(CH$_2$)$_5$), 2.45 (S, 3H, CH$_3$-Het), 2.97 (t, J=9 Hz, 2H, CH$_2$-Het), 3.41 (t, J=9 Hz, 2H, CH$_2$-Br), 6.72 (S, 1H, H-Het).

C$_{11}$H$_{18}$BrNS: Analysis found: C, 47.94; H, 6.62; N, 5.03; S, 11.52; Br, 28.89. Required: C, 47.83; H, 6.57; N, 5.07; S, 11.60; Br, 28.93.

EXAMPLE 40

6-(4-methylisothiazol-5-yl)-hexyl bromide (40)

R = 4-methylisothiazol-5-yl
n = 6.
Light yellow oil, (52%).

NMR (CDCl$_3$) 1.39–2.21 (m, 8H, -(CH$_2$)$_4$), 2.31 (S, 3H, CH$_3$-Het), 2.90 (t, J=9 Hz, 2H, CH$_2$-Het), 3.53 (t, J=9 Hz, 2H, CH$_2$-Br), 8.29 (S, 1H, H-Het).

C$_{10}$H$_{16}$BrNS: Analysis found: C, 45.93; H, 6.15; N, 5.34; S, 12.23; Br, 30.47. Required: C, 45.81; H, 6.19; N, 5.30; S, 12.16, Br, 30.42.

EXAMPLE 41

6-(3,5-dimethylpyrazol-1-yl)hexyl bromide (41)

R = 3,5-dimethylpyrazol-1-yl
n = 6.
Yellow oil, (20%).

NMR (CDCl$_3$) 1.24–2.10 (m, 8H, -(CH$_2$)$_4$), 2.28 (S, 3H, CH$_3$-Het), 3.43 (t, J=9 Hz, 2H, CH$_2$-Het), 4.01 (t, J=9 Hz, 2H, CH$_2$-Br), 5.82 (S, 1H, H-Het).

C$_{11}$H$_{19}$BrN$_2$: Analysis found: C, 51.03; H, 7.43; N, 10.78; Br, 30.76. Required: C, 51.97; H, 7.39; N, 10.81; Br, 30.83.

EXAMPLE 42

6-(isothiazol-5-yl)hexyl bromide (42)

R = isothiazol-5-yl
n = 6.
Yellow oil, (35%).

NMR (CDCl$_3$) 1.16–2.20 (m, 8H, -(CH$_2$)$_4$), 2.97 (t, J=9 Hz, 2H, CH$_2$-Het), 3.43 (t, J=9 Hz, 2H, CH$_2$-Br), 7.01 (S, C$_4$-H, H-Het), 8.40 (S, C$_3$-H, H-Het).

C$_9$H$_{14}$BrNS: Analysis found: C, 43.63; H, 5.74; N, 5.61; S, 12.86; Br, 32.16. Required: C, 43.56; H, 5.69; N, 5.64; S, 12.92; Br, 32.19.

EXAMPLE 43

6-(4-methylthiazol-2-yl)hexyl bromide (43)

R = 4-methylthiazol-2-yl
n = 6.
Yellow oil, (32%).

NMR (CDCl$_3$) 1.00–2.17 (m, 8H, -(CH$_2$)$_4$), 2.42 (S, 3H, CH$_3$-Het), 3.00 (t, J=9 Hz, 2H, CH$_2$-Het), 3.43 (t, J=9 Hz, 2H, CH$_2$-Br), 6.87 (S, 1H, H-Het).

C$_{10}$H$_{16}$BrNS: Analysis found: C, 45.70; H, 6.11; N, 5.39; S, 12.18; Br, 30.42. Required: C, 45.81; H, 6.15; N, 5.34; S, 12.23; Br, 30.47.

EXAMPLE 44

3-(isothiazol-5-yl)propyl bromide (44)

R = isothiazol-5-yl
n = 3.
Yellow oil, (52%).

NMR (CDCl$_3$) 1.98–2.49 (9, J=4 Hz, 2H, -CH$_2$-), 2.96–3.60 (m, 4H, CH$_2$-Het and CH$_2$-Br), 7.05 (S, C$_4$-H, H-Het), 8.40 (S, C$_3$-H, H-Het).

C$_6$H$_8$BrNS: Analysis found: C, 35.07; H, 3.96; N, 6.75; S, 15.50; Br, 38.72. Required: C, 34.97; H, 3.91; N, 6.79; S, 15.56; Br, 38.77.

EXAMPLE 45

1-(1-phenylpyrazol-5-yl)-6-bromohexane (45)

R = 1-phenylpyrazol-5-yl
n = 6.
Yellowish oil, (50%).

NMR (CDCl$_3$) 1.20–2.01 (m, 8H, -(CH$_2$)$_4$); 2.75 (t, J=9 Hz, 2H, CH$_2$-Het), 3.35 (t, J=9 Hz, 2H, CH$_2$-Br), 6.25 (S, 1H, H$_4$-Het), 7.50 (S, 5H, phenyl protons), 7.62 (S, 1H, H$_3$-Het).

C$_{15}$H$_{19}$BrN$_2$: Elemental analysis found: C, 58.75; H, 6.31; N, 9.01. Required: C, 58.64; H, 6.23; N, 9.12.

EXAMPLE 46

1-(imidazol-1-yl)-5-bromohexane (46)

R = imidazol-1-yl
n = 6.
Pale yellowish oil, (50%).

NMR (CDCl$_3$) 1.00–2.10 (m, 8H, -(CH$_2$)$_4$), 3.34 (t, J=9 Hz, 2H, CH$_2$-imidazole), 3.90 (t, J=9 Hz, 2H, CH$_2$-Br), 6.80–7.09 (d, J=18 Hz, 2H, H$_4$ and H$_5$ of imidazole), 7.43 (S, 1H, H$_2$ of imidazole).

C$_9$H$_{15}$BrN$_2$: Analysis found: C, 46.89; H, 6.58; N, 12.06; Br, 34.47. Required: C, 46.77; H, 6.54; N, 12.12; Br, 34.57.

EXAMPLE 47

1-(4-chloro-1-phenyl pyrazol-5-yl)-6-bromohexane (47)

R = 4-chloro-1-phenyl pyrazol-5-yl
n = 6.
Yellowish oil, (48%), IR (neat) 780 cm$^{-1}$ C-Cl; 630 cm$^{-1}$ C-Br.

NMR (CDCl₃), 7.62 (S, 1H, H-pyrazole); 7.3–7.5 (m, 5H, H-phenyl); 3.30 (t, J=9 Hz, 2H, CH$_2$-Br); 2.65 (t, J=9 Hz, 2H, CH$_2$-pyrazole) 1.2–1.75 (m, 8H, 4-CH$_2$-).

$C_{15}H_{18}N_2ClBr$: Analysis found: C, 52.84; H, 5.36; N, 8.17. Required: C, 52.73; H, 5.31; N, 8.20.

ANTI-RHINOVIRUS ACTIVITY EXPERIMENTS

The experiments were performed by a cytopathic effect inhibition method and a neutral red dye uptake assay adapted from the method for activity against Herpes Simplex virus developed by M. Nixon Ellis, Ch. 18 Clinical Virology Manual - Specter, S. Lancz, G. (1986).

Materials:

WI38 cells (source ATCC).

Rhinovirus Types: 1A, 1B, 2, 4, 15, 17, 23, 29, 30, 31, 32, 36, 39, 44, 49, 53, 56, 63, 86, 88 (source ATCC).

Minimum essential medium, Eagle (modified with Earles salt) supplemented with 10% fetal bovine serum, 100 iuml$^{-1}$ penicillin G, 100 gml$^{-1}$ streptomycin and non-essential aminoacids (Sigma M2025).

Drugs dissolved in DMSO to 20 mg ml$^{-1}$ and further diluted in the 10% FBS-MEM.

P.B.S. at pH 6.0.

Citrate/methanol buffer (0.1M citric acid, 157.7 ml; 0.1M sodium citrate, 92.5 ml; dionised H$_2$O 250 ml and methanol, 500 ml).

Neutral red dye.

PROCEDURE

50 µl of each concentration of drug was added (in duplicate) to wells of a 96 well plate. Three wells per plate had medium instead of drug as cell or virus control. The wells were seeded with 100 µl of WI38 cells at $8.0 \times 10^5$ cells ml$^{-1}$. 50 µl of virus was added to each well at a dilution (usually 10 TCID$_{50}$) which would give 100% cytopathic effect after 3 days. A control plate was always set up in parallel to which no virus had been added. The plates were incubated at 33° C. in a 95% air/5% CO$_2$ humidified atmosphere for 3-4 days. When 100% c.p.e. had developed (3-4 days) the cpe/toxic effect was first scored visually using an inverted microscope. The drug concentration at which virus growth was inhibited by 50% was called the minimum inhibitory concentration (MIC$_{50}$). The toxic concentration was calculated by noting the concentration at which there was a change in morphology in 25% of the cells compared to cell controls.

The plates were then subjected to the dye uptake assay. The plates were washed with phosphate buffered saline (P.B.S.) at pH 6.0. Then 250 µl of 0.025% Neutral red/PBS pH 6.0 was added per well and incubated for 45 minutes at 37° C.

The plates were then washed again with PBS pH 6.0 and 250 µl of citrate-methanol buffer was added per well and incubated for 60 minutes at 37° C. The plates were then read on a multiscan spectrophotometer with a 540 mm filter. The cell control was denoted 100% and relative to this the concentration of drug inhibiting virus growth by 50% was called MIC$_{50}$. If the concentration of the drug inhibited cell growth by 25% it was referred to as toxic.

It will be noted that the results obtained by the cytopathic effect inhibition method and the dye uptake method were usually identical, if not the higher of the two values was cited.

The selected compounds of this invention were tested against HRV-1A and HRV-39. The test results are shown in Table I given herebelow.

TABLE I

Toxicity and Activity (MIC$_{50}$) of Some Compounds (µgml$^{-1}$)

| Compound No. | Toxicity | Rhinovirus 1A | Rhinovirus 39 |
|---|---|---|---|
| WIN 51711 (Disoxaril*) | 50 | 10 | 5 |
| 3 | 750 | 50 | 50 |
| 5 | 100 | 5 | 1 |
| 6 | >50 | 50 | 50 |
| 8 | 25 | 10 | 10 |
| 9 | 50 | 5 | 1 |
| 10 | 50 | 25 | 25 |
| 11 | 50 | 25 | 10 |
| 12 | 50 | 25 | 10 |
| 13 | 50 | 25 | 10 |
| 14 | >50 | 25 | 25 |
| 15 | 50 | 10 | 5 |
| 16 | 25 | NA | 5 |
| 18 | >50 | 25 | 25 |
| 19 | 50 | 10 | 5 |
| 21 | 50 | 25 | 10 |
| 22 | >50 | 25 | 25 |
| 25 | 50 | 10 | 5 |
| 27 | 50 | 10 | 10 |
| 29 | >50 | NA | 25 |
| 30 | >50 | 10 | 5 |
| 31 | 25 | 10 | 10 |
| 32 | 50 | 25 | 25 |

M.I.C. = Minimum inhibitory concentration
N.A. = Not active

Those compounds showing activity comparable to DISOXARIL have been tested against twenty serotypes of Rhinoviruses (HRV-1A, 1B, 2, 4, 15, 17, 23, 29, 30, 31, 32, 36, 39, 44, 49, 53, 56, 63, 86, 88) to evaluate the range of activity in comparison therewith. The results are summarized in Table II, given herebelow.

TABLE II

Toxicity and Activity (MIC 50) of Some Compounds (ugml$^{-1}$)

| Compound No. | 5 | 8 | 9 | 15 | 19 | 25 | 27 | 30 | Disoxaril WIN 51711 |
|---|---|---|---|---|---|---|---|---|---|
| Toxicity | 100 | 25 | 50 | 50 | 50 | 50 | 50 | >50 | 50 |
| Rhinovirus Type: | | | | | | | | | |
| 1A* | 5 | 10 | 5 | 10 | 10 | 10 | 10 | 10 | 25 |
| 1B* | 5 | 5 | 10 | 5 | 5 | 5 | 5 | 10 | 25 |
| 2* | NA | — | 1 | NA | 10 | 20 | NA | — | NA |
| 4* | <0.5 | NA | 10 | 1 | NA | NA | 25 | 10 | 0.5 |
| 15* | 5 | NA | 5 | 5 | 10 | 10 | 10 | 5 | 5 |
| 17 | 10 | NA | NA | 5 | NA | 10 | 10 | — | <0.5 |
| 23 | 5 | — | 5 | 10 | 10 | 5 | 5 | — | 10 |
| 29* | 5 | NA | 5 | 5 | 10 | 5 | 25 | — | 10 |
| 30 | 0.5 | — | 0.5 | 5 | 0.5 | 10 | 10 | — | 0.5 |
| 31* | 10 | 1 | 1 | 1 | NA | NA | 10 | NA | 25 |
| 32 | 25 | — | 10 | NA | NA | 10 | 10 | — | 10 |

TABLE II-continued

Toxicity and Activity (MIC 50) of Some Compounds (ugml$^{-1}$)

| Compound No. | 5 | 8 | 9 | 15 | 19 | 25 | 27 | 30 | Disoxaril WIN 51711 |
|---|---|---|---|---|---|---|---|---|---|
| 36 | NA | NA | 10 | NA | NA | NA | NA | — | NA |
| 39 | 1 | 10 | 5 | 5 | 5 | 5 | 10 | 5 | 5 |
| 44 | <0.5 | — | 1 | 1 | <0.5 | 5 | 10 | — | <0.5 |
| 49 | NA | — | 10 | NA | NA | NA | NA | — | NA |
| 53 | 10 | — | 5 | NA | 10 | 10 | 10 | — | 25 |
| 56 | 5 | — | 5 | 5 | 10 | 10 | 5 | — | 25 |
| 63 | 10 | — | 5 | NA | 10 | 5 | 25 | — | 25 |
| 86 | 0.5 | NA | 5 | <0.5 | 10 | 10 | 1 | — | 0.5 |
| 88 | 0.5 | — | <0.5 | <0.5 | 1 | 10 | NA | — | <0.5 |
| All Rhinovirus Serotypes | 17/20 | 4/10 | 19/20 | 14/20 | 14/20 | 16/20 | 17/20 | 5/6 | 17/20 |

NA = No activity (at 25 ugml)
— = Not tested
MIC 50 = Minimum Inhibitory Concentration, 50%
*Seven commonest serotypes Further experiments regarding the active antirhinovirus agents, mentioned in Table II, were carried out to determine the activity of these compounds against other picornaviruses. The selected compounds were tested against Polio-I, Coxsacki-A9; Coxsacki-A21; Coxsacki-B1; Coxsacki-B4; Echo-7; and Echo-11 viruses, and the results are summarized in Table III, given herebelow.

TABLE III

Toxicity and Activity (MIC 50) of Some Compounds (ugml$^{-1}$)

| Compound No. | 5 | 8 | 9 | 15 | 19 | 25 | 27 | Disoxaril (WIN 51711) |
|---|---|---|---|---|---|---|---|---|
| Toxicity | 100 | 25 | 50 | 50 | 50 | 50 | 50 | 50 |
| Enterovirus Type: | | | | | | | | |
| Polio 1 | 10 | NA | NA | 5 | NA | 10 | NA | 5 |
| Cox. A9 | 5 | — | NA | 1 | 10 | 10 | 5 | 5 |
| Cox. A21 | 5 | NA | 10 | 5 | 10 | 5 | 10 | 5 |
| Cox. B1 | 10 | NA | NA | 25 | 5 | NA | 10 | 10 |
| Cox. B4 | NA | — | 10 | 10 | NA | NA | NA | 10 |
| Echo 7 | 25 | NA | NA | 10 | 25 | 5 | NA | 5 |
| Echo 11 | NA | NA | NA | NA | NA | NA | NA | 5 |
| All Enterovirus Serotypes | 5/7 | 0/5 | 2/7 | 6/7 | 4/7 | 4/7 | 3/7 | 7/7 |

NA = No activity (at 25 μgml)
— = Not tested
MIC 50 = Minimum Inhibitory Concentration, 50%

In summary, the compounds of this invention can be utilized in the prevention or treatment of common cold, aseptic meningitis, encephalitis, hepatitis, myocarditis, meningoencephalitis, and upper respiratory illnesses caused by the coxsacki viruses.

The embodiments of the invention in which an exclusive property or privilege is claimed are defined as follows:

1. A heteroaryloxyalkylheterocycle of the Formula I

R—(CH$_2$)$_n$—O—R$^1$     I wherein

R is a non-fused azole moiety selected from the group consisting of:
3-methyl-5-isoxazolyl; 4-methylthiazol-2-yl; 4-methylisothiazol-5-yl; 3,5-dimethylpyrazol-1-yl; 1-phenylpyrazol-5-yl; 4-chloro-1-phenylpyrazol-5-yl; 5-isothiazolyl and 1-imidazolyl, n is 5, 6, 7 or 8 and R$^1$ is selected from the group consisting of 1-naphthyl; 2-naphthyl; 1-benzotriazolyl; naphth-(1,2-b)-1,4-oxazin-4-yl; N-dibenzylamino; 4-(1,2,4-triazol-1-yl)-phenyl; 2-benzoxazolyl; 4-(imidazol-1-yl)phenyl; 2-benzofuryl; 1-bornyl; 1-adamantanyl; 4-methylquinolin-2-yl; 2-methylquinoline-4-yl; 2-benzimidazolyl; fluoren-9-yl; 2-carbazolyl and 4-acridyl.

2. A heteroaryloxyalkylheterocycle according to claim 1, wherein n is 6 or 7.

3. 5-{7-[4-(imidazol-1-yl)phenoxy]heptyl}-3-methylisoxazole according to claim 1.

4. 5-{7-[(benzoxazol-2-yl)oxy]heptyl}-3-methylisoxazole according to claim 1.

5. 5-{7-[4-(1,2,4-triazol-1-yl)phenoxy]heptyl}-3-methylisoxazole according to claim 1.

6. 5-[7-(N,N-dibenzylaminoxy)heptyl]-3-methylisoxazole according claim 1.

7. 5-[7-(2-dibenzofuroxy)heptyl]-3-methylisoxazole according to claim 1.

8. 5-[7-(2,3-dihydro-3-oxo-4H-naphth[1,2-b]-1,4-oxazine-4-yl)oxyheptyl]-3-methylisoxazole according to claim 1.

9. 1-[6-(benzotriazol-1-yl)oxyhexyl]-3,5-dimethylpyrazole according to claim 1.

10. 5-[7-(carbazol-2-yl)oxyheptyl]-3-methylisoxazole according to claim 1.

11. 5-[7-(2-methylquinolin-4-yl)oxyheptyl]-3-methylisoxazole according to claim 1.

12. 5-[7-(4-methylaquinolin-2-yl)oxyheptyl]-3-methylisoxazole according to claim 1.

13. 5-[7-(benzimidazol-2-yl)oxyheptyl]-3-methylisoxazole according to claim 1.

14. 5-[7-(adamantan-1-yl)oxyheptyl]-3-methylisoxazole according to claim 1.

15. 5-[7-(2-naphthyl)oxyheptyl]-3-methylisoxazole according to claim 1.

16. 5-[7-(1-naphthyl)oxyheptyl]-3-methylisoxazole according to claim 1.

17. 2-[7-(2-dibenzofuroxy)heptyl]-4-methylthiazole according to claim 1.

18. 2-[7-(2-methylquinolin-4-yl)oxyheptyl]-4-methylthiazole according to claim 1.

19. 2-[7-(4-methylquinolin-2-yl)oxyheptyl]-4-methylthiazole according to claim 1.

20. 2-[7-(2-naphthyl)oxyheptyl]-4-methylthiazole according to claim 1.

21. 5-[6-(2-dibenzofuroxy)hexyl]-4-methylisothiazole according to claim 1.

22. 5-[6-(2-methylquinolin-4-yl)oxyhexyl]-4-methylisothiazole according to claim 1.

23. 5-[6-(2-naphthyl)oxyhexyl]-4-methylisothiazole according to claim 1.

24. 5-[6-(1-naphthyl)oxyhexyl]-4-methylisothiazole according to claim 1.

25. 1-[6-(2,3-dihydro-3-oxo-4H-naphth[1,2-b]-1,4-oxazine-4-yl)oxyhexyl]-3,5-dimethylpyrazole according to claim 1.

26. 1-[6-(2-dibenzofuroxy)hexyl]-3,5-dimethylpyrazole according to claim 1.

27. 5-[6-(2-dibenzofuroxy)hexyl]isothiazole according to claim 1.

28. 5-[6-(2-methylquinolin-4-yl)oxyhexyl]isothiazole according to claim 1.

29. 2-[6-(2-dibenzofuroxy)hexyl]-4-methylthiazole according to claim 1.

30. 5-[3-(2-methylquinolin-4-yl)oxypropyl]isothiazole according to claim 1.

31. 5-[7-(fluorene-9-yl)oxyheptyl]-3-methylisoxazole according to claim 1.

32. 5-[6-(2-dibenzofuroxy)hexyl]-1-phenylpyrazole according to claim 1.

33. 5-[6-(2-methylquinolin-4-yl)oxyhexyl]-1-phenylpyrazole according to claim 1.

34. 5-[6-(2-naphthyl)oxyhexyl]-1-phenylpyrazole according to claim 1.

35. 5-[6-(1-naphthyl)oxyhexyl]-1-phenylpyrazole according to claim 1.

36. 1-[6-(2-methylquinolin-4-yl)oxyhexyl]-imidazole according to claim 1.

37. 4-chloro-5-[6-(2-methylquinolin-4-yl)oxyhexyl]-phenylpyrazole according to claim 1.

38. 4-chloro-5-(6-(carbazol-2-yl)oxyhexyl]phenylpyrazole according to claim 1.

39. 4-chloro-5-[6-(2-dibenzofuroxy)hexyl]phenylpyrazole according to claim 1.

* * * * *